United States Patent
Mukasa

(10) Patent No.: US 9,031,372 B2
(45) Date of Patent: May 12, 2015

(54) HOLEY FIBER AND METHOD OF PRODUCING THE SAME

(71) Applicant: Furukawa Electric Co., Ltd., Tokyo (JP)

(72) Inventor: Kazunori Mukasa, Tokyo (JP)

(73) Assignee: Furukawa Electric Co., Ltd., Tokyo (JP)

( * ) Notice: Subject to any disclaimer, the term of this patent is extended or adjusted under 35 U.S.C. 154(b) by 0 days.

(21) Appl. No.: 14/203,019

(22) Filed: Mar. 10, 2014

(65) Prior Publication Data

US 2014/0193128 A1 Jul. 10, 2014

Related U.S. Application Data

(63) Continuation of application No. PCT/JP2013/060871, filed on Apr. 10, 2013.

(30) Foreign Application Priority Data

May 24, 2012 (JP) ................................. 2012-118738

(51) Int. Cl.
*G02B 6/02* (2006.01)
*G01N 21/3504* (2014.01)
*G01N 21/03* (2006.01)

(52) U.S. Cl.
CPC ........ *G02B 6/02357* (2013.01); *G02B 6/02338* (2013.01); *G02B 6/02347* (2013.01); *G02B 6/02385* (2013.01); *G01N 21/3504* (2013.01); *G01N 2021/0346* (2013.01)

(58) Field of Classification Search
CPC .................... G02B 6/02338; G02B 6/02357
USPC .................................................. 385/124, 125
See application file for complete search history.

(56) References Cited

U.S. PATENT DOCUMENTS 5,155,792 A * 10/1992 Vali et al. ...................... 385/125
6,418,258 B1 * 7/2002 Wang ............................ 385/125
(Continued)

FOREIGN PATENT DOCUMENTS

JP 2003-040637 A 2/2003
JP 2004-294654 A 10/2004
(Continued)

OTHER PUBLICATIONS

English Translation of Matsui et al, A Photonic Crystal Fiber With Enlarged Effective Area and Flat Dispersion, Nen IEICE, p. 247, 2004.*
International Search Report mailed May 14, 2013 for PCT/JP2013/060871 filed Apr. 10, 2013 with English Translation.
International Written Opinion mailed May 14, 2013 for PCT/JP2013/060871 filed Apr. 10, 2013.
(Continued)

*Primary Examiner* — Ryan Lepisto
(74) *Attorney, Agent, or Firm* — Oblon, McClelland, Maier & Neustadt, L.L.P.

(57) ABSTRACT

A holey fiber includes: a core portion; an inner-cladding portion positioned at an outer periphery of the core portion, the inner-cladding portion having a plurality of inner holes formed in a layered structure around the core portion; and an outer-cladding portion positioned at an outer periphery of the inner-cladding portion, the outer-cladding portion having a plurality of outer holes formed in a layered structure around the inner-cladding portion. The inner holes are disposed to form a triangular lattice of which lattice constant $\Lambda 1$ is equal to or smaller than 2.0 μm and to form equal to or greater than two layers. The outer holes are disposed to form a triangular lattice of which lattice constant $\Lambda 2$ is greater than the $\Lambda 1$ and equal to or larger than 3.0 μm and to form equal to or greater than two layers. The overlap index is equal to or greater than 2.0%.

10 Claims, 4 Drawing Sheets

(56) References Cited

U.S. PATENT DOCUMENTS

| | | | | |
|---|---|---|---|---|
| 6,972,894 | B2* | 12/2005 | Bjarklev et al. | 359/332 |
| 7,116,875 | B2* | 10/2006 | Wadsworth et al. | 385/123 |
| 2001/0028775 | A1 | 10/2001 | Hasegawa et al. | |
| 2004/0005127 | A1* | 1/2004 | Kliner et al. | 385/114 |
| 2005/0069269 | A1* | 3/2005 | Libori et al. | 385/125 |

FOREIGN PATENT DOCUMENTS

| | | |
|---|---|---|
| JP | 2005-017650 A | 1/2005 |
| JP | 2006-053331 A | 2/2006 |
| JP | 2006-243423 A | 9/2006 |
| JP | 2007-041426 A | 2/2007 |
| JP | 2012-014081 A | 1/2012 |
| WO | WO 01/63328 A1 | 8/2001 |

OTHER PUBLICATIONS

Takashi Matsui, et al., "A photonic crystal fiber with enlarged effective area and flat dispersion", 2004 Nen IEICE Electronics Society Taikai Koen Ronbunshu 1, Sep. 8, 2004, C-3-115, p. 247.

John A. Jay, "Low Signal Latency in Optical Fiber Networks" Proceeding of $60^{th}$ IWCS Conference, International Wire & Cable Symposium, 2011, pp. 429-437.

W. Belardi, et al., "A 10GBIT/S Tuneable Wavelength Converter Based on Four-Wave Mixing in Highly Nonlinear Holey Fibre", ECOC 2002, pp. 1-2.

K. Mukasa et al., "Novel fabrication method of highly-nonlinear silica holey fibres" CLEO-US 2006 CMC5, pp. 1-2.

Takashi Matsui et al., "Dispersion-Flattened Photonic Crystal Fiber With Large Effective Area and Low Confinement Loss" Journal of Lightwave Technology, vol. 23, No. 12, Dec. 2005, pp. 4178-4183.

* cited by examiner

HOLEY FIBER AND METHOD OF PRODUCING THE SAME

CROSS-REFERENCE TO RELATED APPLICATION

This application is a continuation of PCT International Application No. PCT/JP2013/060871 filed on Apr. 10, 2013 which claims the benefit of priority from Japanese Patent Application No. 2012-118738 filed on May 24, 2012, the entire contents of which are incorporated herein by reference.

BACKGROUND OF THE INVENTION

1. Field of the Invention

The present invention relates to a holey fiber and a method of producing the same.

2. Description of the Related Art

Conventionally, a holey fiber having a holey structure has been expected to be applied to a sensor. For example, when a holey fiber is used as a gas-cell, and in case that gas exists, inside of a hole is filled with the gas. Since, in a holey fiber, a field of propagating light and the hole overlap, a part of light leaking into the hole is absorbed by the gas. For example, in case of methane gas, light at a wavelength of 1491 nm is absorbed by the gas. It can be used as a gas sensor by detecting the absorption of gas. Many articles exist for such a gas sensor.

On the other hand, in a field of financial market, it is required to conduct a greater amount of processing in response to a processing request in a short period of waiting time i.e. at low latency, and this requirement is gaining more attention as a future important attempt. For example, J. A. Jay, "Low Signal Latency in Optical Fiber Networks" Proceeding of 60th IWCS, pp. 429-437, (2011). proposes a method of restraining delay of signal transmission with various approaches for a low-latency system and notes an optical fiber transmission line, in which overlapping of an optical field and a hole is increased, as an extremely important transmission path.

SUMMARY OF THE INVENTION

It is an object of the present invention to at least partially solve the problems in the conventional technology.

In accordance with one aspect of the present invention, there is provided a holey fiber which includes: a core portion; an inner-cladding portion positioned at an outer periphery of the core portion, the inner-cladding portion having a plurality of inner holes formed in a layered structure around the core portion; and an outer-cladding portion positioned at an outer periphery of the inner-cladding portion, the outer-cladding portion having a plurality of outer holes formed in a layered structure around the inner-cladding portion. The inner holes are disposed to form a triangular lattice of which lattice constant $\Lambda 1$ is equal to or smaller than 2.0 µm and to form equal to or greater than two layers. The outer holes are disposed to form a triangular lattice of which lattice constant $\Lambda 2$ is greater than the $\Lambda 1$ and equal to or larger than 3.0 µm and to form equal to or greater than two layers. The overlap index is equal to or greater than 2.0%.

In accordance with another aspect of the present invention, there is provided a method of producing a holey fiber by using a stack-and-draw method. The holey fiber includes: a core portion; an inner-cladding portion positioned at an outer periphery of the core portion, the inner-cladding portion having a plurality of inner holes formed in a layered structure around the core portion; and an outer-cladding portion positioned at an outer periphery of the inner-cladding portion, the outer-cladding portion having a plurality of outer holes formed in a layered structure around the inner-cladding portion. The inner holes are disposed to form a triangular lattice of which lattice constant $\Lambda 1$ is equal to or smaller than 2.0 µm and to form equal to or greater than two layers. The outer holes are disposed to form a triangular lattice of which lattice constant $\Lambda 2$ is greater than the $\Lambda 1$ and equal to or larger than 3.0 µm and to form equal to or greater than two layers. The overlap index is equal to or greater than 2.0%.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Hereinafter, embodiments of a holey fiber and a method of producing the same according to the present invention will be explained in detail with reference to the drawings. It should be noted that the invention is not limited by these embodiments. In addition, terms not defined in this specification is subject to definition and measurement method in International Telecommunication Union (ITU-T) G.650. 1.

As a holey fiber in which overlapping of an optical field with a hole is increased, holey fibers disclosed in W. Belardi et al., "A 10 GBIT/S TUNEABLE WAVELENGTH CONVERTER BASED ON FOUR-WAVE MIXING IN HIGHLY NONLINEAR HOLEY FIBRE" ECOC 2002, PD1.2, (2002). and K. Mukasa et al., "Novel fabrication method of highly-nonlinear silica holey fibres" CLEO-US 2006, CMC5, (2006). are proposed.

However, the holey fiber disclosed in the articles is designed so that holes each having a large hole diameter are disposed around a core having a small cross-sectional area to increase the overlapping by increasing the field leaking into the holes while confining light sufficiently. Such design includes a problem that producing a favorable structure is difficult since cross-sectional area shape of the hole or the core tends to be distorted.

In contrast, according to the present embodiments, a holey fiber which is easy to produce and in which a field of light overlaps with holes to a great extent is obtained.

Figure 1A:
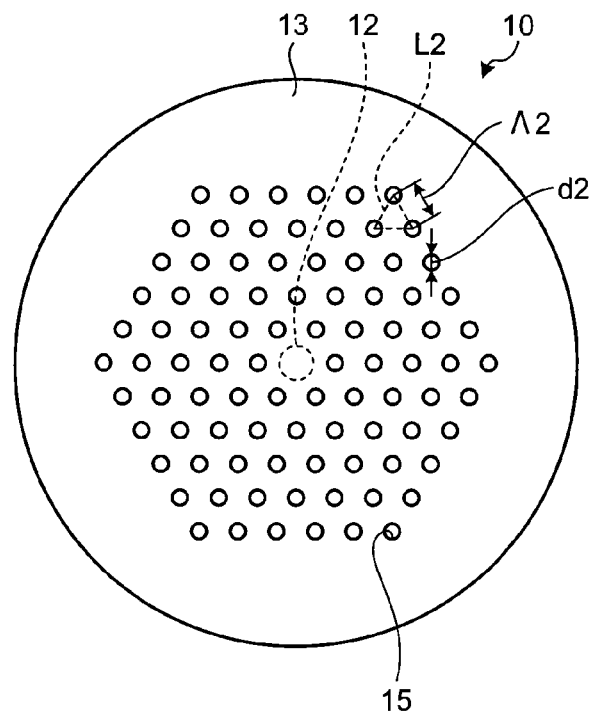
FIG. 1A is a schematic view showing a cross-sectional structure of a holey fiber according to an embodiment.
Figure 1B:
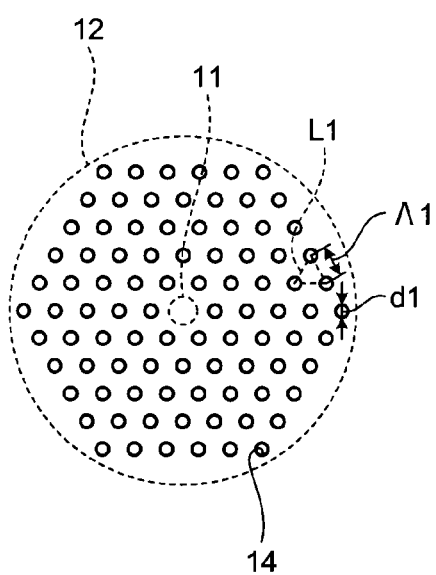
FIG. 1B is an enlarged view showing a cross-sectional structure of an inner-cladding portion of the holey fiber shown in FIG. 1A.

FIG. 1A is a schematic view showing a cross-sectional structure of a holey fiber according to an embodiment of the present invention. As shown in FIG. 1A, a holey fiber 10 includes an inner-cladding portion 12 and an outer cladding portion 13 positioned at an outer periphery of the inner-cladding portion 12. FIG. 1B is an enlarged view showing a cross-sectional structure of the inner-cladding portion of the holey fiber shown in FIG. 1A. As shown in FIG. 1B, the holey fiber 10 further includes a core portion 11, and the inner-cladding portion 12 is positioned at an outer periphery of the core portion 11. Every one of the core portion 11, the inner-cladding portion 12, and the outer cladding portion 13 is made of pure silica glass which is not doped with refractive-index-adjusting dopant.

The core portion 11 has a solid structure which has no hole formed thereinside. The inner-cladding portion 12 has a plurality of inner holes 14 formed around the core portion 11. The inner holes 14 are disposed to form a triangular lattice L1 and form a layer structure where the inner holes 14 disposed on each apex and each side of a regular hexagon of which the core portion 11 is centered form one layer. In the holey fiber 10, the inner holes 14 form a five-layer structure.

When d1 indicates a hole diameter of the inner hole 14 and Λ1 indicates a lattice constant of the triangular lattice L1 (that is, inter-hole distance), d1/Λ1 is set at 0.45. In addition, Λ1 is set at 2.0 μm.

The outer cladding portion 13 has a plurality of outer holes 15 formed around the inner-cladding portion 12. The outer holes 15 are disposed to form a triangular lattice L2 and form a layer structure where the outer holes 15 disposed on each apex and each side of a regular hexagon of which the core portion 11 is centered form one layer. In the holey fiber 10, the outer holes 15 hereby form a five-layer structure.

When d2 indicates a hole diameter of the outer hole 15 and Λ2 indicates a lattice constant of the triangular lattice L2, d2/Λ2 is set at 0.45. In addition, Λ2 is set at 4.0 μm.

Since herein both d1/Λ1 of the inner holes 14 and d2/Λ2 of the outer holes 15 are 0.45, the holey fiber 10 satisfies an endlessly single mode (ESM) condition. It should be noted that ESM means that a cut-off wavelength does not exist and a single mode optical propagation is realized at a wide wavelength band.

In addition, since Λ1 of the inner holes 14 of the holey fiber 10 is 2.0 μm and relatively small, and since the inner holes 14 are of the, relatively great number of, five-layer structure, overlapping of the field of light propagating primarily in the core portion 11 of the holey fiber 10 with the inner holes 14 disposed around the core portion 11 is great. Therefore, the holey fiber 10 is suitable for an optical fiber for use of a sensor or a low-latency system.

Herein, when making the overlapping increase by decreasing Λ1 in this manner, since confinement of light by the inner holes 14 is weakened, confinement loss may increase.

In contrast to this, in the holey fiber 10, the outer holes 15 are disposed at an outer periphery of the inner holes 14. In the outer holes 15, since Λ2 is 4.0 μm and greater than Λ1, and since the outer holes 15 are in the, relatively great number of, five-layer structure, light is confined sufficiently by the outer holes 15. As a result of this, the confinement loss of the holey fiber 10 is small to a degree of equal to or lower than $1 \times 10^{-2}$ dB/km, for example.

In addition, since the holey fiber 10 is of a structure that the holes form a triangular lattice, a highly accurate structure can be produced easily by using a publicly-known stack-and-draw method or a hole-drilling method.

For example, in case of using a publicly-known stack-and-draw method, a first preform (also referred to as core cane) to form the core portion 11 and the inner-cladding portion 12 is formed by using the stack-and-draw method. After that, a second preform to form the outer cladding portion 13 having the outer holes 15 is formed by disposing (stacking) a glass tube at an outer periphery of the first preform. After that, by drawing an optical fiber from the second preform, the holey fiber 10 can be produced.

Hereafter, a preferable aspect of the holey fiber 10 according to the present embodiment will be explained more specifically with reference to a result of calculation using a simulation by finite element method. It should be noted that, in the calculation, a triangular lattice-type holey fiber which is defined by a hole diameter d and a lattice constant Λ as structural parameters was used. In addition, the wavelength of light was set at 1550 nm.

To begin with, a preferable value of d/Λ will be explained. It is preferable that the holey fiber 10 satisfies the ESM condition.

Figure 2:
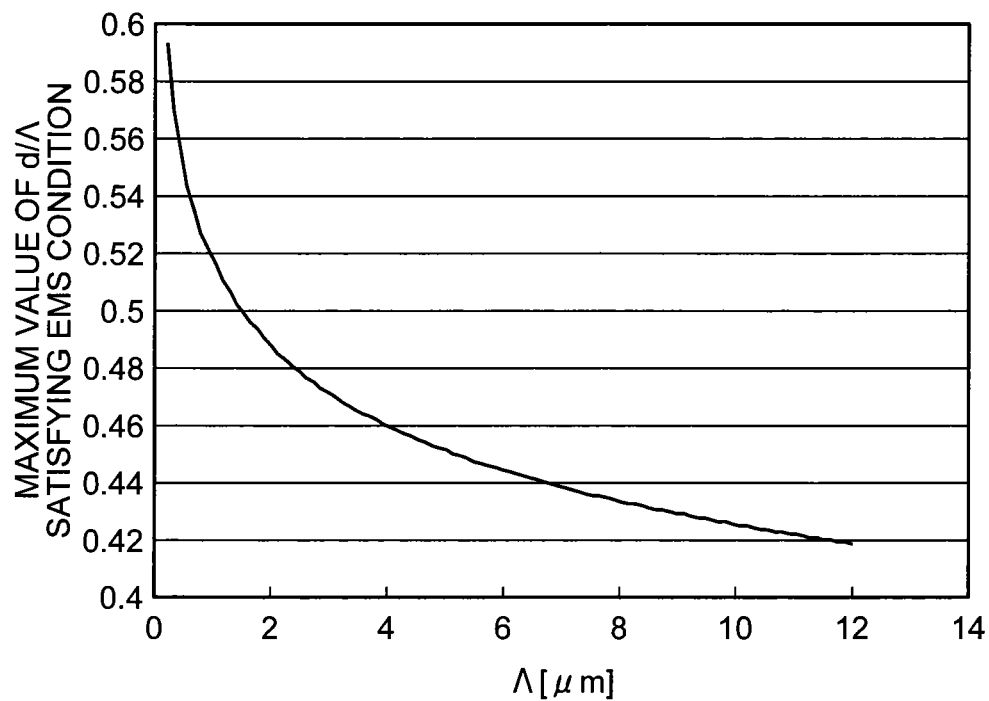
FIG. 2 is a drawing showing a relationship between $\Lambda$ and the maximum value of $d/\Lambda$ satisfying an ESM condition.

FIG. 2 is a drawing showing a relationship between Λ and the maximum value of d/Λ satisfying the ESM condition. In case that d/Λ for a certain value of Λ is equal to or smaller than the maximum value of d/Λ shown in FIG. 2, the ESM condition is satisfied. As shown in FIG. 2, even though Λ is small, the ESM condition is not satisfied unless d/Λ is equal to or smaller than 0.6. In the holey fiber 10, it is also preferable to satisfy the ESM condition by making the d1/Λ1 and d2/Λ2 equal to or smaller than 0.6, or more preferably, equal to or smaller than 0.55.

Next, a relationship between d/Λ and overlap index for different Λs were studied in case that the holes are of the five-layer structure. Herein the overlap index is defined as a ratio of intensity of field of light overlapping with the holes relative to the total of intensity of field of light propagating through the holey fiber.

Figure 3:
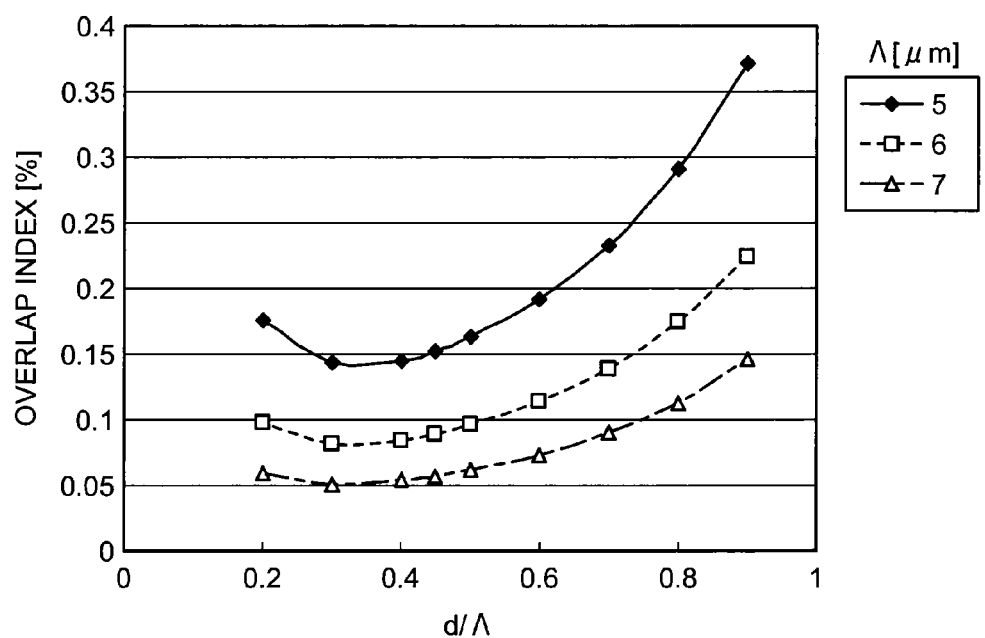
FIG. 3 is a drawing showing a relationship between $d/\Lambda$ and an overlap index for different $\Lambda$s.

FIG. 3 is a drawing showing a relationship between d/Λ and the overlap index for different Λs. It was found that, as shown in FIG. 3, if Λ is great to some degree, the overlap index changes very little even if the value of d/Λ is changed.

Then, hereafter a relationship between Λ and the overlap index was studied by fixing d/Λ at the value of 0.45, which satisfies the ESM condition even if Λ is approximately 3.0 μm (see FIG. 2). It should be noted that, the number of layers of the holes was set at two, three, four, or five.

Figure 4:
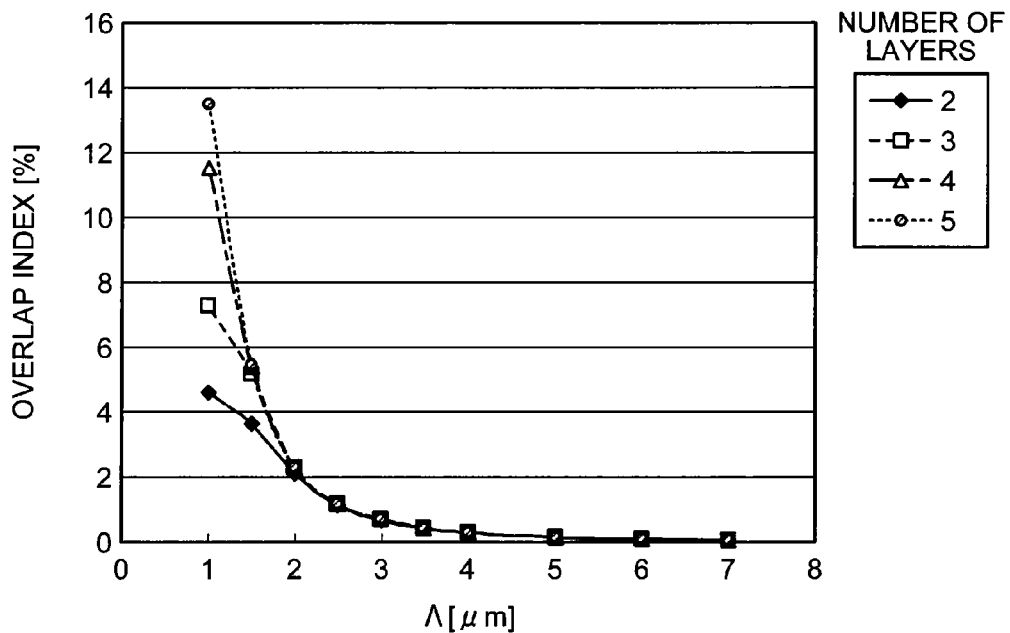
FIG. 4 is a drawing showing a relationship between $\Lambda$ and the overlap index for different number of layers.

FIG. 4 is a drawing showing a relationship between Λ and the overlap index for different number of layers. As shown in FIG. 4, when Λ is smaller than 3.0 μm, the overlap index increases sharply. For example, in case that Λ was equal to or smaller than 3.0 μm, the overlap index was equal to or greater than approximately 0.5%; in case that Λ was equal to or smaller than 2.5 μm, the overlap index was equal to or greater than approximately 1.0%; and in case that Λ was equal to or smaller than 2.0 μm, the overlap index was equal to or greater than approximately 2.0%. In addition, in case that Λ was 1.0 μm and the number of layers was equal to or greater than four, the overlap index was great, i.e., equal to or greater than 10%.

Therefore, in order to increase the overlap index, it is preferable that the Λ1 of the inner holes 14 is equal to or smaller than 3.0 μm, it is more preferable that the Λ1 is equal to or smaller than 2.5 μm, and it is further more preferable that the Λ1 is equal to or smaller than 2.0 μm. In addition, the more number of layers of the inner holes 14, i.e. equal to or greater than three layers, is preferable, and the number of layers of the inner holes 14 equal to or greater than four layers is further more preferable.

Figure 5:
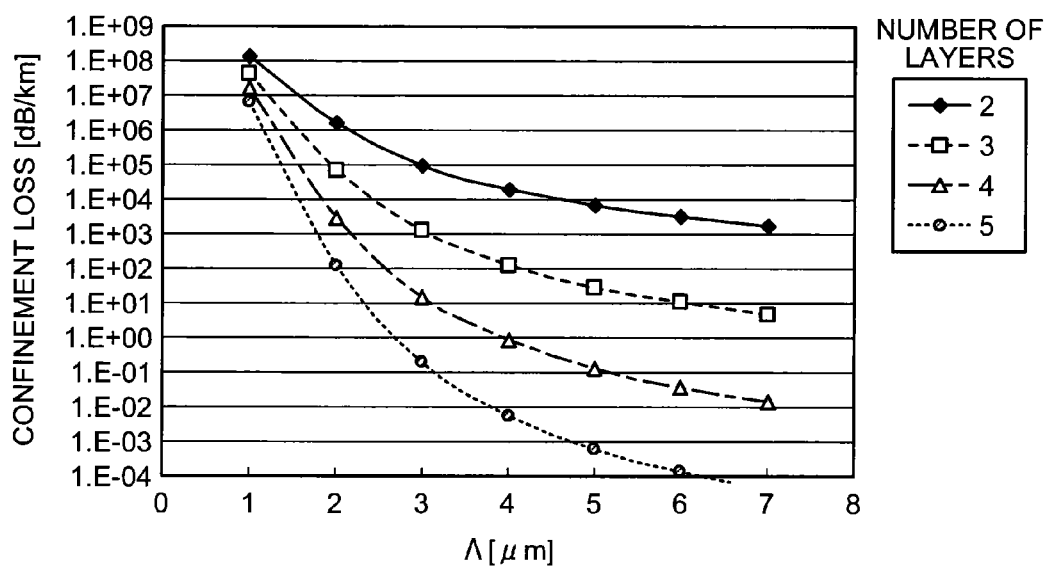
FIG. 5 is a drawing showing a relationship between $\Lambda$ and confinement loss for different number of layers.
Figure 6:
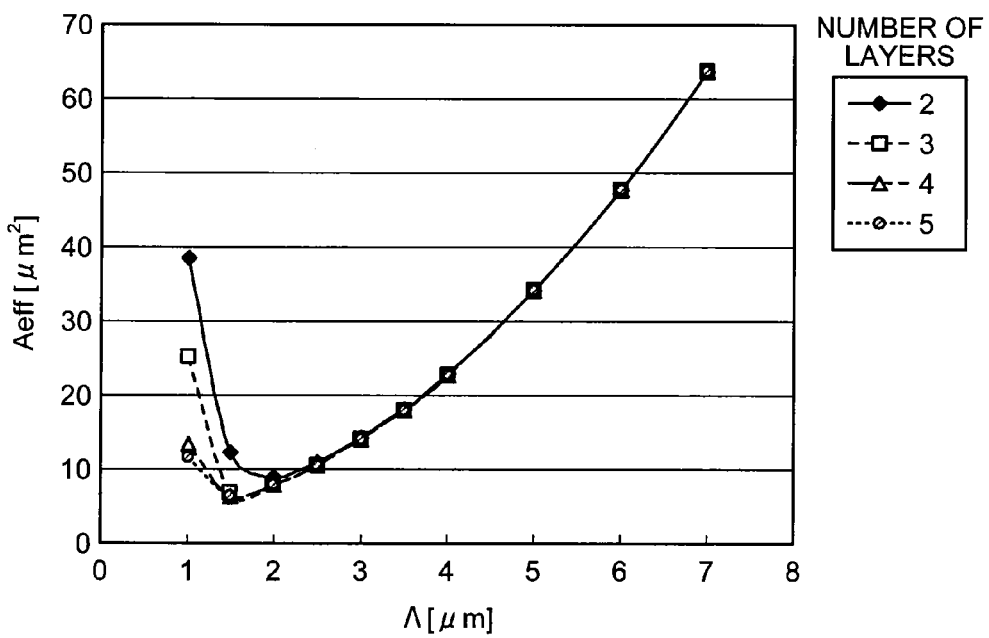
FIG. 6 is a drawing showing a relationship between $\Lambda$ and effective core area for different number of layers.

On the other hand, for the outer holes 15, it is preferable that the Λ2 is set so that confinement loss is small. FIG. 5 is a drawing showing a relationship between Λ and confinement loss for different number of layers. It should be noted that d/Λ is 0.45. As shown in FIG. 5, along with decrease in Λ, the confinement loss increases exponentially. In addition, when increasing the number of layers, the confinement loss decreases. In addition, FIG. 6 is a drawing showing a relationship between Λ and effective core area ($A_{eff}$) for different number of layers. In FIG. 6, when Λ decreases and is lower than approximately 1.5 µm, $A_{eff}$ increases sharply. The reason for that is considered that the degree of confining light weakened sharply.

For example, in case of using a holey fiber as a sensor, it is preferable that confinement loss is equal to or lower than 1 dB/m (1×10³ dB/km). In order to realize this, for the outer holes 15, it is preferable that Λ2 is equal to or larger than 3.0 µm. In addition, the more number of layers of the outer holes 15, i.e. equal to or greater than three layers, is preferable, and the number of layers of the outer holes 15 equal to or greater than four layers is further more preferable.

In addition, for example, in case of using a holey fiber as a signal transmission path, it is preferable that confinement loss is equal to or lower than 1 dB/km. In order to realize this, for the outer holes 15, it is preferable that Λ2 is equal to or larger than 3.0 µm, and it is further more preferable that l12 is equal to or larger than 4.0 µm. In addition, for the number of layers of the outer holes 15, it is preferable to be equal to or greater than four layers, and it is further preferable to be equal to or greater than five layers.

In addition, when increasing the number of holey layers, the total number of the holes to be formed increases sharply. It is further preferable that the number of layers of either ones of the inner holes 14 and the outer holes 15 is approximately equal to or smaller than 5 since the total number of holes to be formed can be restrained, and thus the productivity of the holey fiber increases.

As a wavelength of light propagating through the holey fiber according to the present invention, a wavelength corresponding to a wavelength band such as 1300 nm to 1600 nm used for signal light in optical fiber transmission or a wavelength corresponding to a wavelength of light absorbed by a gas to be detected can be used appropriately according to purpose.

It should be noted that, although d/Λ of the holey fiber of the above-described embodiment is set to satisfy the ESM condition, the present invention is not limited to this, and the d/Λ not satisfying the ESM condition may be set to propagate light in multi-mode at a certain wavelength.

In addition, the above-described embodiment does not limit the present invention. The above-described respective elements combined appropriately are included in the present invention. In addition, further effects or modification examples can be derived by an ordinary skilled person in the art easily. Therefore, further wide aspects of the present invention are not limited by the above-described embodiment and can be modified variously.

As described above, the holey fiber and the method of producing the same according to the present invention are preferable for use for a sensor or optical communication.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A holey fiber comprising:
    a core portion;
    an inner-cladding portion positioned at an outer periphery of the core portion, the inner-cladding portion having a plurality of inner holes formed in a layered structure around the core portion; and
    an outer-cladding portion positioned at an outer periphery of the inner-cladding portion, the outer-cladding portion having a plurality of outer holes formed in a layered structure around the inner-cladding portion, wherein
    the inner holes are disposed to form a triangular lattice of which lattice constant Λ1 is equal to or smaller than 2.0 µm and to form equal to or greater than two layers,
    the outer holes are disposed to form a triangular lattice of which lattice constant Λ2 is greater than the Λ1 and equal to or larger than 3.0 µm and to form equal to or greater than two layers, and
    the overlap index is equal to or greater than 2.0%.

2. The holey fiber according to claim 1, wherein number of the layers of the inner holes is equal to or greater than three.

3. The holey fiber according to claim 2, wherein the number of the layers of the inner holes is equal to or greater than four.

4. The holey fiber according to claim 1, wherein number of the layers of the outer holes is equal to or greater than three.

5. The holey fiber according to claim 4, wherein the number of the layers of the outer holes is equal to or greater than four.

6. The holey fiber according to claim 1, wherein confinement loss is equal to or lower than 1 dB/m.

7. The holey fiber according to claim 6, wherein the confinement loss is equal to or lower than 1 dB/km.

8. The holey fiber according to claim 1, wherein d1/Λ1 and d2/Λ2 are equal to or smaller than 0.6 where d1 [µm] indicates diameter of the inner holes and d2 [µm] indicates diameter of the outer holes.

9. A method of producing a holey fiber by using a stack-and-draw method, the holey fiber comprising:
    a core portion;
    an inner-cladding portion positioned at an outer periphery of the core portion, the inner-cladding portion having a plurality of inner holes formed in a layered structure around the core portion; and
    an outer-cladding portion positioned at an outer periphery of the inner-cladding portion, the outer-cladding portion having a plurality of outer holes formed in a layered structure around the inner-cladding portion, wherein
    the inner holes are disposed to form a triangular lattice of which lattice constant Λ1 is equal to or smaller than 2.0 µm and to form equal to or greater than two layers,
    the outer holes are disposed to form a triangular lattice of which lattice constant Λ2 is greater than the Λ1 and equal to or larger than 3.0 µm and to form equal to or greater than two layers, and
    the overlap index is equal to or greater than 2.0%.

10. The method of producing the holey fiber according to claim 9, comprising:
    forming a first preform to form the core portion and the inner-cladding portion by using the stack-and-draw method;
    forming a second preform to form the outer-cladding portion having the outer holes by disposing a glass tube at an outer periphery of the first preform; and
    drawing the holey fiber from the second preform.

* * * * *